United States Patent [19]
Heaton et al.

[11] Patent Number: 5,797,538
[45] Date of Patent: Aug. 25, 1998

[54] ARTICULATING APPARATUS FOR APPLYING SURGICAL FASTENERS TO BODY TISSUE

[75] Inventors: Lisa W. Heaton, Norwalk; Mitchell J. Palmer, New Milford; Keith L. Milliman, Bethel, all of Conn.; Richard C. McClure, Claremont, Calif.

[73] Assignee: United States Surgical Corporation, Norwalk, Conn.

[21] Appl. No.: 815,632

[22] Filed: Mar. 13, 1997

Related U.S. Application Data

[63] Continuation of Ser. No. 318,593, Oct. 5, 1994, abandoned.

[51] Int. Cl.⁶ .................................................. A61B 17/068
[52] U.S. Cl. ...................... 227/176.1; 227/19; 227/179.1
[58] Field of Search ........................ 227/19, 175.1, 227/176.1, 178.1, 179.1

[56] References Cited

U.S. PATENT DOCUMENTS

| | | |
|---|---|---|
| 3,892,228 | 7/1975 | Mitsui . |
| 4,207,873 | 6/1980 | Kruy . |
| 4,688,555 | 8/1987 | Wardle . |
| 4,728,020 | 3/1988 | Green et al . |
| 4,880,015 | 11/1989 | Nierman . |
| 4,938,408 | 7/1990 | Bedi et al. . |
| 5,018,657 | 5/1991 | Pedlick et al. . |
| 5,271,543 | 12/1993 | Grant et al. ................. 227/19 |
| 5,312,023 | 5/1994 | Green et al. . |
| 5,318,221 | 6/1994 | Green et al. . |
| 5,348,259 | 9/1994 | Blanco et al. ............... 227/19 |
| 5,381,943 | 1/1995 | Allen et al. ................. 227/19 |
| 5,431,323 | 7/1995 | Smith et al. ................ 227/19 |
| 5,482,197 | 1/1996 | Green et al. ................ 227/19 |
| 5,485,952 | 1/1996 | Fontayne .................... 227/19 |
| 5,605,273 | 2/1997 | Hamblin et al. ............ 227/19 |

FOREIGN PATENT DOCUMENTS

0324637  7/1989  European Pat. Off. .

*Primary Examiner*—Scott A. Smith

[57] ABSTRACT

Apparatus for applying a plurality of surgical fasteners to body tissue includes an elongated body extending from a handle assembly. A fastener cartridge housing pivotably connected to a distal portion of the elongated body receives a fastener cartridge containing a plurality of surgical fasteners. A fastener driving mechanism actuatable from the handle assembly ejects fasteners from the fastener cartridge to form them against an anvil mounted adjacent the cartridge housing. The fastener cartridge is pivotably movable from a position in alignment with a longitudinal axis of the elongated body to a position out of alignment with the elongated body. Visual indication of the relative position of the fastener cartridge is provided by a control lever which is movable toward and away from the handle assembly to correspond with movement of the fastener cartridge. A clamp mechanism is also provided to move the anvil relative to the cartridge housing to clamp tissue therebetween.

16 Claims, 8 Drawing Sheets

FIG_1

FIG. 2

ARTICULATING APPARATUS FOR APPLYING SURGICAL FASTENERS TO BODY TISSUE

This is a continuation of application Ser. No. 08/318,593 filed on Oct. 5,1994 now abandoned.

BACKGROUND

1. Technical Field

The technical field relates to a surgical apparatus, and more particularly to a surgical stapling apparatus that can perform operations such as articulation, tissue clamping, staple forming and/or tissue cutting.

2. Background of Related Art

Surgical stapling instruments are known wherein tissue is first grasped or clamped between opposing jaw structure and then fastened by means of fasteners. In some instruments a knife is provided to cut tissue which has been joined by the fasteners. The fasteners are typically in the form of surgical staples, however, two part polymeric type fasteners are also known.

Instruments for this purpose can include two elongated jaws which are respectively used to capture or clamp tissue. Typically, one of the jaws carries a disposable cartridge wherein a plurality of staples are arranged in at least two lateral rows while the other jaw has an anvil for forming the staple legs as the staples are driven from the cartridge. Generally, the stapling operation is effected by a camming element which travels longitudinally through the cartridge carrying member and acts upon individual staple pushers to sequentially eject the staples from the cartridge. A knife can be positioned in such a manner so as to operate sequentially immediately behind the camming element and laterally positioned between the staple rows to longitudinally cut and/or open the stapled tissue between the rows of staples. Such instruments are disclosed in Bobrov et al. (U.S. Pat. No. 3,079,606) and Green '675 (U.S. Pat. No. 3,490,675).

A later instrument disclosed in U.S. Pat. No. 3,499,591 to Green applies a double row of staples on each side of the incision. This is accomplished by a cartridge assembly wherein a cam member moves within an elongate guide path between two sets of staggered staple carrying grooves. Staple drive members are positioned in such a manner so as to be contacted by the longitudinally moving cam to effect ejection of the staples. The cartridge assemblies typically come in a plurality of sizes, each varying in both length and number of staples contained therein. Depending on the procedure to be performed, the surgeon must select the appropriate cartridge assembly.

The instruments described above were all designed for use in surgical procedures wherein surgeons have direct access to the operation site. However, in endoscopic or laparoscopic procedures, surgery is performed through a small incision or through narrow cannulae inserted through entrance wounds in the skin. In order to address the specific needs of endoscopic and/or laparoscopic surgical procedures, endoscopic surgical stapling devices such as those disclosed in U.S. Pat. No. B5,040,715 and U.S. Pat. No. 5,318,221, both to Green et al., have been developed. In general, these instruments are provided with clamping structure to effect approximation of an anvil and a staple cartridge to secure tissue therebetween, and staple firing structure to effect sequential ejection of a plurality of staples from the staple cartridge after the tissue has been secured.

Many of the instruments described above are limited in their range of operability. Improvements, however, have been made in the art of surgical instruments to provide increased range of operability. For example, U.S. Pat. Nos. 5,312,023 and 5,326,013, both to Green et al., are directed to a surgical apparatus having a mechanism for effectuating the articulation of a fastener applying assembly disposed at a distal end of the instrument. The mechanism to effectuate articulation includes a rotatable dial member operatively associated with the exterior of the elongated tubular section and is connected to a cable loop or linkage which effects articulation. By turning the dial, the fastener applying assembly at the distal end of the instrument can be caused to articulate, i.e., bend away from the longitudinal axis of the instrument.

While the dial concept is useful, it would be helpful to provide the surgeon with an external articulation actuator mechanism that is movable in a manner that externally indicates the state of articulation of the fastening and cutting portion of the instrument relative to the elongated tubular shaft of the instrument. In laparoscopic procedures, such a mechanism would permit the surgeon to know the state of articulation without having to check video monitors. It would also be beneficial to provide an instrument including an actuation control member which is more readily and conveniently accessible to the user and which is easier to control during surgical procedures.

SUMMARY

An apparatus is provided for applying a plurality of surgical fasteners to body tissue which includes a handle assembly and an elongated body extending from the handle assembly and defining a longitudinal axis. A cartridge housing is also provided and is pivotably connected to a distal end portion of the elongated body. The cartridge housing is configured to receive a fastener cartridge containing a plurality of surgical fasteners therein. The apparatus also includes an anvil mounted adjacent the cartridge housing and defining a fastener forming surface against which surgical fasteners are driven when ejected from the fastener cartridge. A fastener driving mechanism is provided in operative association with the fastener cartridge and is actuatable from the handle assembly to eject fasteners from the fastener cartridge.

A linkage mechanism is operatively associated with the cartridge housing to pivotably move the cartridge housing between a first position in alignment with the longitudinal axis of the elongated body, and a second position out of alignment with the longitudinal axis. A control lever, which provides external visual indication to the user of the relative position of the cartridge housing with respect to the elongated body, is operatively connected to the linkage mechanism and movable between a first position corresponding to the first position of the cartridge housing and a second position corresponding to the second position of the cartridge housing.

Alternative features of the apparatus include the elongated body being rotatably disposed relative to the handle body and a clamping mechanism operatively associated with the anvil to move the anvil relative to the cartridge housing and to clamp tissue therebetween. In one preferred embodiment, the clamping mechanism includes a plurality of elongated flexible bands which flex upon movement of the cartridge housing from the first position to the second position. The flexible bands permit clamping while the instrument is articulated or in the second position. The clamping mechanism can further include a cam operatively associated with the anvil and the plurality of elongated bands.

The fastener driving mechanism also preferably includes a plurality of elongated flexible bands which flex upon movement of the cartridge housing from the first position to the second position. The flexible bands permit firing while the instrument is articulated or in the second position. A camming member may be included in the fastening firing mechanism, which is adapted to urge the fasteners from the fastener cartridge. Preferably the camming member moves in a distal direction to urge the fasteners from the fastener cartridge.

The clamping mechanism of an alternative configuration of the apparatus is actuable from the handle assembly to move the anvil relative to the cartridge housing to clamp tissue therebetween and includes a first link, a reversing member operatively connected to the first link member and having a distal end, a second link operatively connected to the distal end of the reversing member and a pair of pivotably connected clamp fingers, operatively connected to the reversing member. In this configuration, proximal movement of the first link results in distal movement of the second link.

BRIEF DESCRIPTION OF THE DRAWINGS

Various embodiments are described herein with reference to the drawings, wherein.

DETAILED DESCRIPTION OF PREFERRED EMBODIMENTS

It is generally accepted that endoscopic procedures are more common than laparoscopic procedures. Accordingly, the following embodiments shall be discussed in terms of endoscopic procedures and apparatus. However, use herein of terms such as "endoscopic", "endoscopically" and "endoscopic portion", among others, should not be construed to limit the claims appended hereto to a stapling and cutting apparatus for use only in conjunction with an endoscopic tube. On the contrary, it is believed that the embodiments described herein may find use in any procedure where access is limited to a small incision, including but not limited to laparoscopic procedures. Also, as used herein the terms "fasteners" and "staples" shall be treated equivalently. Unless otherwise stated, the term "cartridge assembly" shall include at least the cartridge itself and staples or fasteners and staple drive members disposed therein. In the drawings and the description which follows, as is customary, the term "proximal" refers to the end which is closest to the operator when the instrument is in use, while the term "distal" will refer to the end which is furthest from the operator during use thereof.

Figure 1:
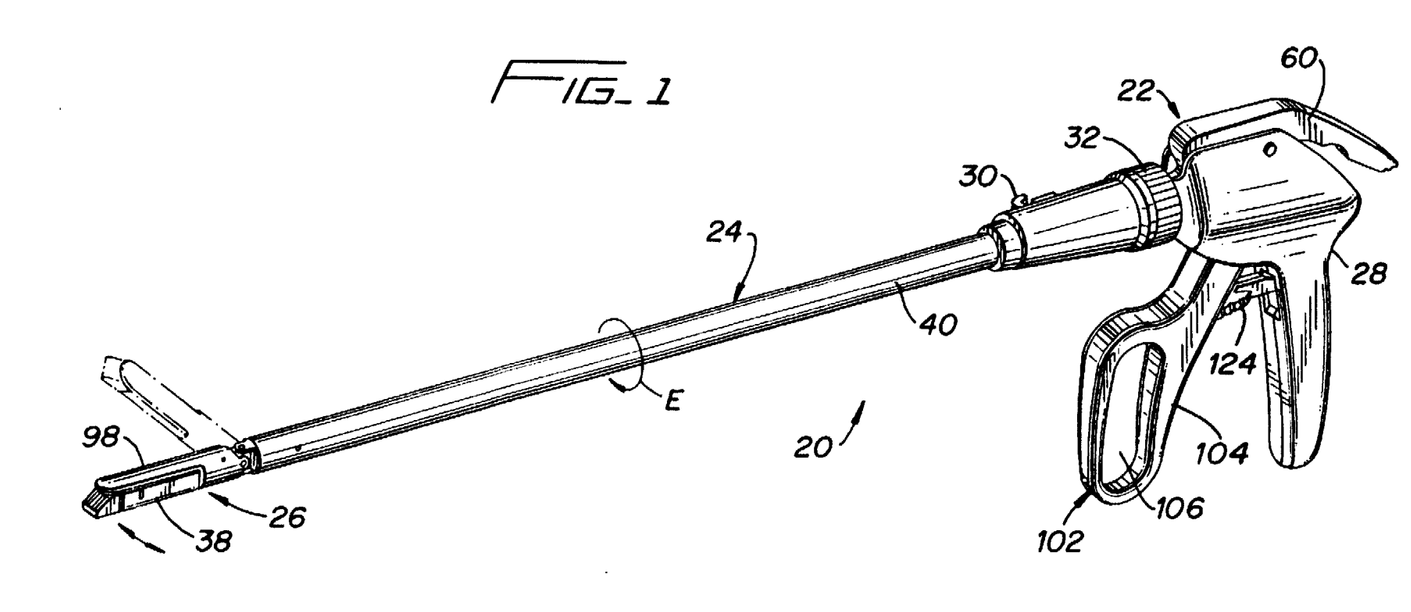
FIG. 1 is a perspective view of a surgical stapling instrument in accordance with the present disclosure.

Preferred embodiments of the surgical stapler will now be described in detail with reference to the drawings, wherein like reference numerals designate identical or corresponding parts throughout the several views. In FIG. 1, a surgical stapler is illustrated and designated generally by reference numeral 20. Surgical stapler 20, as noted above, is configured to engage body tissue, apply a plurality of surgical fasteners thereto, and form an incision in the fastened body tissue during an endoscopic surgical procedure. In brief, surgical stapler 20 includes a handle portion 22, an elongate body portion 24 extending distally from handle portion 22, and a fastening and cutting portion 26 operatively associated with a distal end of body portion 24.

Figure 2:
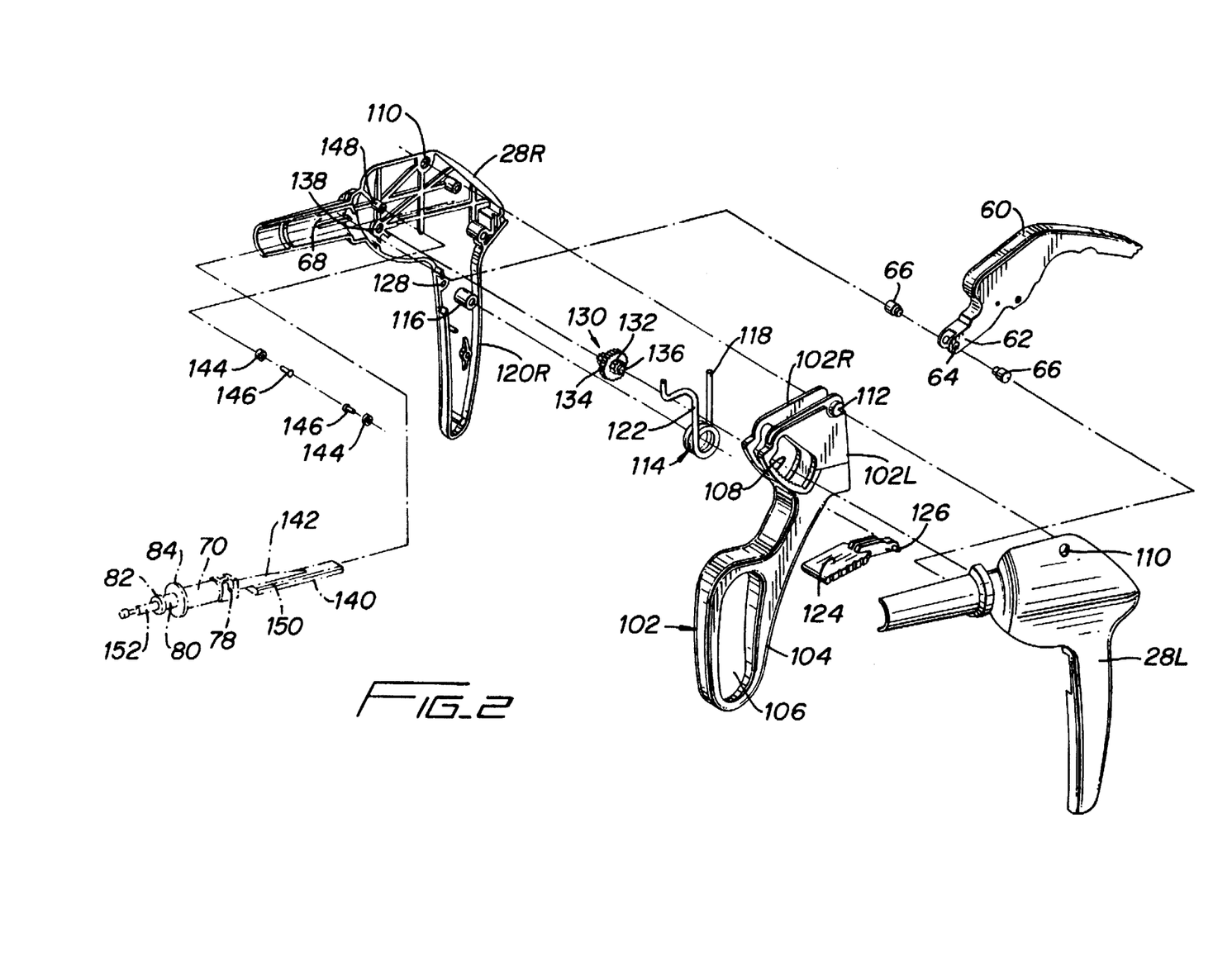
FIG. 2 is a perspective view, with parts separated, of the handle assembly of the instrument of FIG. 1.

Referring to FIG. 2, the handle portion 22 of surgical apparatus 20 is shown and includes a handle body 28 that has two parts, a left body portion 28L and a right body portion 28R. These portions are optimally fastened together by means of ultrasonic welding along the peripheral contacting surfaces thereof, although screws, adhesives, press fit structures or other suitable means of joining the two handle body parts may also be utilized. The handle body 28 is of an overall size and shape convenient for being held in one hand.

The structural elements providing for articulation of fastening and cutting portion 26 and rotation of elongate body portion 24 will now be described with reference to FIGS. 2–4B. Articulation control lever 30 is pivotally mounted to rotation handle 32 such that articulation control lever 30 pivots about pin 34, as shown in FIG. 4B. Actuation control link rod 36 has longitudinal slot 36b and transverse slot 36a. In the unarticulated position, external elongate section 30a of lever 30 is generally parallel with axis "C" of the instrument, as is the axis "C'" of fastening assembly 26. To articulate fastener assembly 26 away from axis "C", lever 30 is pivoted about pin 34. This pivoting action causes pin 35' to slide in transverse slot 36a of rod 36 and further causes rod 36 to move proximally, thereby articulating fastener assembly 26. Slot 36b permits rod 36 to move longitudinally relative to pin 34.

Cartridge housing 38 is pivotally mounted to tube cover 40 by rivet 42 at extended finger portion 44 such that rivet 42 passes through a centrally disposed bore formed through the proximal end of cartridge housing 38. Cartridge housing 38 is pivotally attached at a bore formed therein which is adjacent to the bore which receives rivet 42 to a distal end portion of articulation control link rod 36. In this manner, reciprocal longitudinal motion of articulation control link rod 36 pivots cartridge housing 38 about rivet 42 such that fastening and cutting portion 26 articulates to one side of surgical instrument 20 toward and away from a central longitudinal axis "C" thereof. One preferred configuration for such articulation has provided for a radius of motion a of approximately 30° to 35° measured from the central longitudinal axis "C" of surgical stapler 20.

Additional structural elements are provided to support fastening and cutting portion 26. In particular, a pivot post 46 is mounted near the distal end of cover tube 40, for example, by a pin 48 passing through transverse bores formed in legs 50 extending proximally from pivot post 46 (shown in FIG. 4A). Pivot post 46 preferably includes a shield 52 formed on one side thereof and extending distally therefrom. Shield 52 prevents the creation of a pinch point wherein tissue may become trapped when surgical stapler 52 is moved from the articulated position to the longitudinal aligned position. Also provided are a lower pivot 54, a pivot plate 56 and a support 58 each of which add stability to the pivotally mounted fastening and cutting portion 26.

Rotation handle 32 is an abbreviated frustoconical structure having a central bore formed by the joining of arcuate split sections 32a and 32b. The split sections are preferably ultrasonically welded along the peripheral contacting surfaces thereof, although screws, adhesives, press fit structures or other suitable means of joining the two parts may also be utilized. A pair of longitudinally spaced extended tabs 33 are positioned on an interior facing arcuate collar portion at the distal ends of each of split sections 32a and 32b and engage correspondingly spaced indentations 35 formed oppositely on the exterior surface of cover tube 40. At a proximal end of rotation handle 32, knurling 37 may be provided to facilitate rotation. Because of the engaging structural relationship of the rotation handle 32 and cover tube 40, rotation of handle 32 effects rotation of cover tube 40, indicated by Arrow "E" in FIG. 1 and, therefore, rotation of the articulated fastening and cutting portion 26, as shown in phantom lines also in FIG. 1.

The structural components of the clamp subassembly of surgical stapler 20 will now be described with continued reference to FIGS. 1–3. A clamp approximation control lever 60 is pivotally mounted within handle body 28 for movement between an open position and a closed position. At a distal end, the clamp lever 60 is provided with a fork portion 62 having a pair of transversely aligned apertures 64 for receiving clamp lever pins 66. Pins 66 pass through apertures 64 and interfit in slots 68 formed on the inside wall of body portions 28L and 28R for longitudinal reciprocal movement therein.

A pusher member 70 is provided to interconnect the clamp approximation control lever 60 and a clamp pusher tube 72, such that an elongated bore 74, formed longitudinally through pusher member 70, is in communication with the hollow interior 76 (FIG. 6) of clamp pusher tube 72. A pair of U-shaped indented surfaces 78 are formed near a distal end of pusher member 70 and are sized to loosely receive pins 66 for free rotation of same.

Pusher member 70 has a longitudinally, distally extending reduced diameter end portion 80 with a plug 82 formed at a distal end thereof. End portion 80 is inserted into the open proximal end of clamp pusher tube 72. Pusher member 70 has a flange 84 which is secured to the proximal end of clamp pusher tube 72 by, for example, welding, bonding or other suitable known techniques. In this manner, reciprocal longitudinal motion of clamp pusher tube 72 is induced by raising and lowering clamp approximation control lever 60. Alternatively, plug 82 may be of such diameter as to provide for a friction fit within the interior wall of clamp pusher tube 72.

Figures 5, 5A:
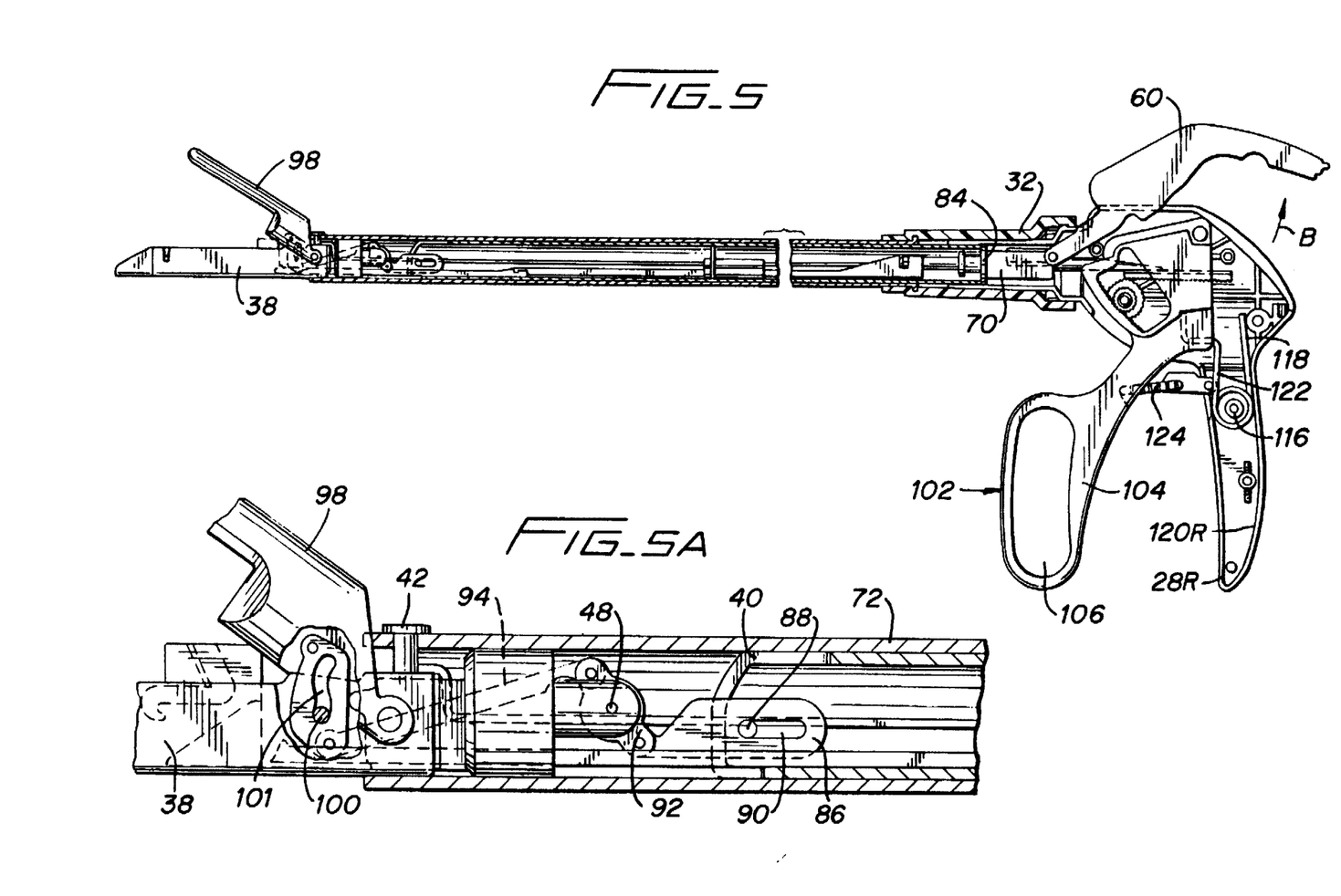
FIG. 5 is a side cross-sectional view, which illustrates the various components of the clamp actuation structure.
FIG. 5A is an enlarged, partial cross-sectional view of the distal end of the stapling instrument, which illustrates the reverser link and clamp cam.

A clamp link 86 is interconnected with clamp pusher tube 72 by a pin 88 inserted through a transverse bore formed at the distal end of clamp pusher tube 72 and passing through longitudinal slot 90 (shown in FIG. 5A). Slot 90 allows pusher tube 72 to travel a predetermined distance before causing movement of clamp link 86, as will be described in detail below.

Figure 4:
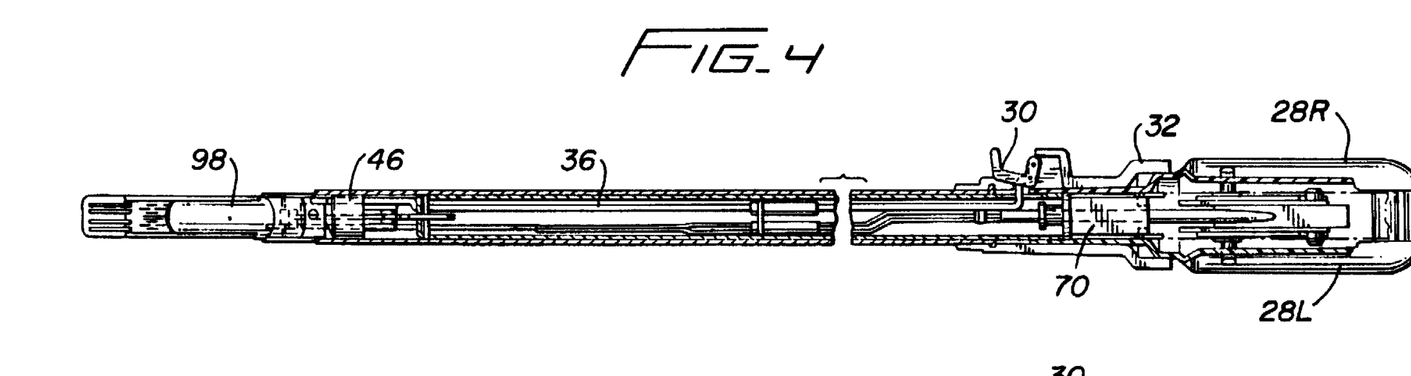
FIG. 4 is a top cross-sectional view which illustrates the articulation control structural components of the instrument of FIG. 1.
Figure 4A:
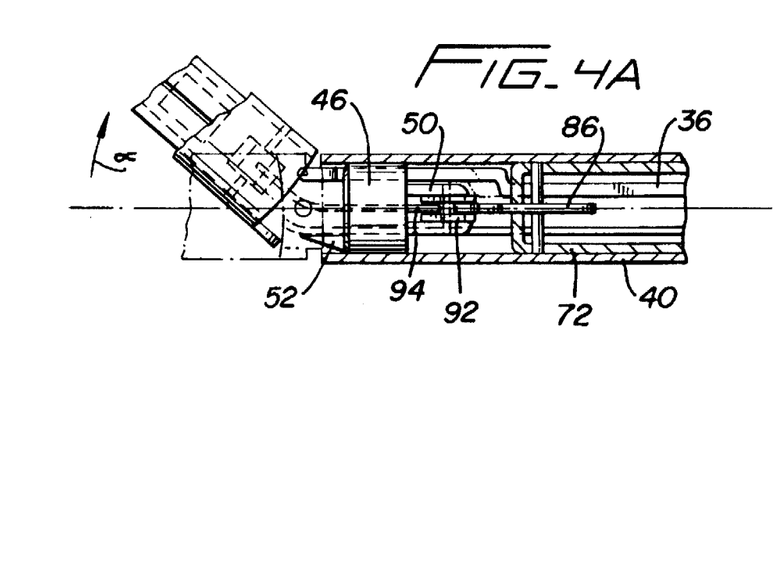
FIGS. 4A and 4B are enlarged partial cross-sectional views, which illustrate the articulation capability of the fastening and cutting portion and the associated control lever positions of the instrument of FIG. 1, respectively.

A reverser link 92 is pivotally mounted to tube cover 40 by pin 48, interfitted between legs 50 of pivot post 46 (as shown in FIG. 4A). Reverser link 92 pivots about a point on surgical stapler 20 which is fixed relative to handle body 28. Reverser link 92 is further pivotally connected at one end to a distally extending portion of link 86 and at the other end to laterally stacked flexible clamp links 94. Flexible clamp links 94 are preferably thin bands formed of a resilient flexible material, such as stainless steel or other similar materials, which exhibit similar flexibility and strength characteristics. Upon articulation of fastener and cutting portion 26, flexible pushers 166 and flexible clamp lengths 94 bend to allow for such articulation. In this manner, distal movement of clamp pusher tube 72 is translated by pivoting of reverser link 92 to proximal movement of flexible clamp links 94. Distal end portions of clamp links 94 are pivotally connected to clamp cam 96, which in turn is pivotally interconnected to anvil 98. The motion of clamp cam 96 is governed by camming pin 100 passing through cam slot 101 (FIG. 5A) which is frictionally fitted in a bore formed transversely through cartridge housing 38. Thus, reciprocating motion of clamp pusher tube 72 translates to clamping motion of anvil 98.

Figure 3:
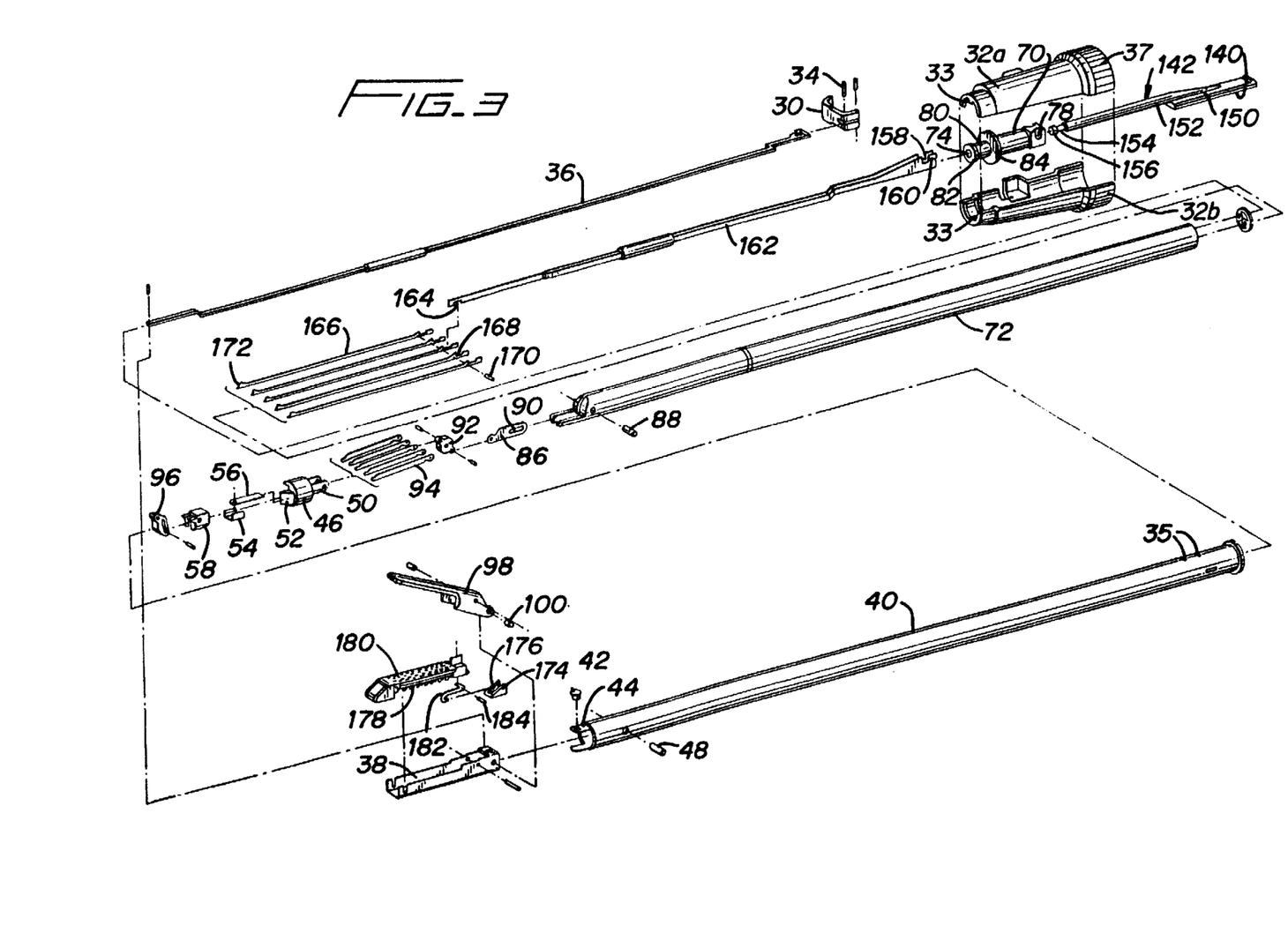
FIG. 3 is a perspective view, with parts separated, of the interior structural components of the various operational features of the instrument of FIG. 1.
Figure 4B:
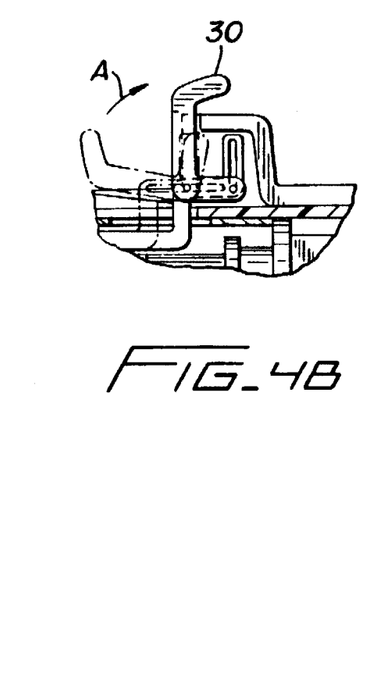

Referring to FIGS. 1–3, a trigger 102 has a shank portion 104 which forms an opening 106 sized to enable the user to grasp shank 104 by inserting a plurality of fingers therein and to facilitate squeezing it in a trigger like fashion. Trigger 102 includes web portions 102L and 102R extending from shank portion 104. Each of web portions 102L and 102R include an aperture formed therein such that, on one internal surface of the aperture, an arcuate rack 108 is formed. Transverse apertures 110 are formed in frame portions 28L and 28R to receive raised pin portions 112 which extend transversely from the upper portion of each of trigger webs 102L and 102R. Thus, trigger 102 pivots within handle body 28 about transverse apertures 110. A coil spring 114 is mounted within body portions 28L and 28R on a transversely extending boss 116 formed on the inside wall of handle body portion 28R. Spring leg 118 biases firmly against a rear wall (FIGS. 5 and 6) of handle body 28, formed by portions 120L and 120R of body portions 28L and 28R, respectively. Spring leg 122 biases trigger 102 away from handle body 28 toward a prefired position (also shown in FIGS. 5 and 6).

With continued reference to FIGS. 1 and 2, a manual safety 124 is provided to lock trigger 102 in the unfired position to prevent accidental retraction thereof. Safety 124 has transverse projections 126 formed on a proximal end thereof, which interfit into receiving holes 128 formed in handle body portions 28L and 28R for pivotal movement of the safety 124 between an engaged position and a disengaged position. In the engaged position, the distal surface of safety 124 frictionally interfits with a receiving surface (shown in phantom lines in FIGS. 5 and 6) formed on the distal surface of trigger 102. To unlock the trigger 102, safety 124 is simply pivoted downward out of engagement with the receiving surface of trigger 102.

A pinion-spur-gear assembly 130, which includes a pinion gear 132 interfitting with a spur gear 134, provides plural driving surfaces, the function of which will be described in detail below. Pinion gear 132 is further provided with projections 136 formed at either end thereof which interfit with holes 138 formed in handle body portions 28L and 28R to facilitate rotational motion of pinion-spur-gear assembly 124 about a transverse axis formed by projections 136.

Figure 7:
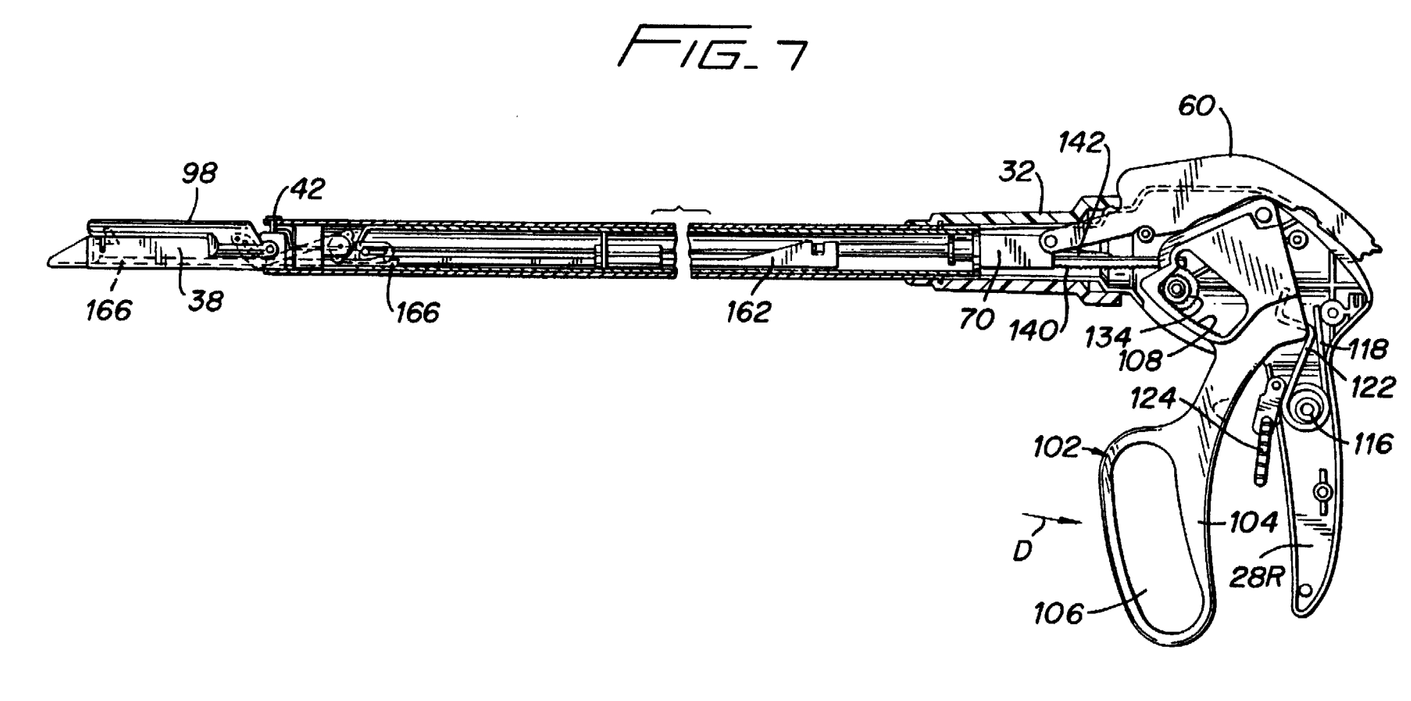
FIG. 7 is a side cross-sectional view, which illustrates actuation of the fastener firing mechanism.
Figure 8:
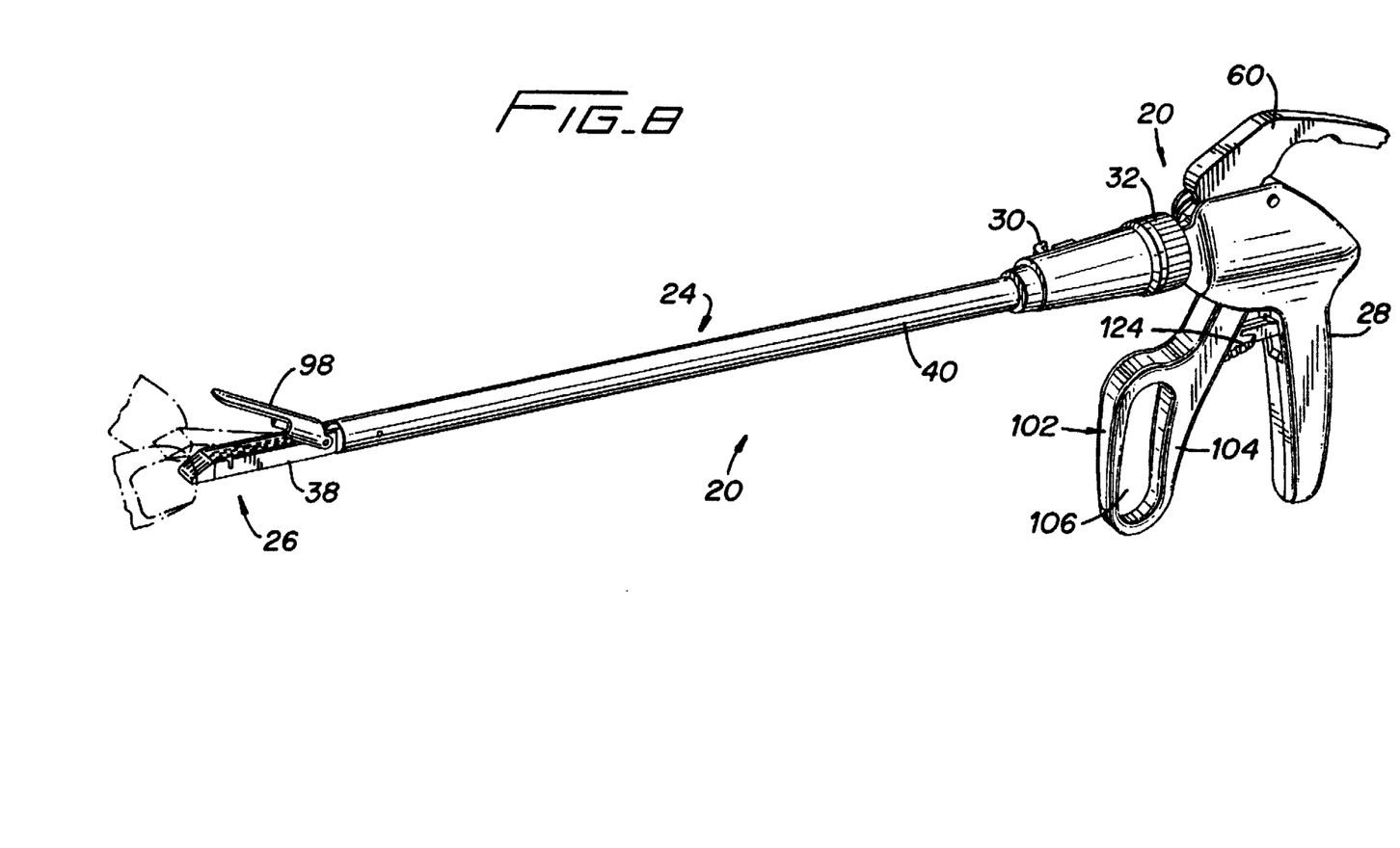
FIG. 8 is a side cross-sectional view, which illustrates replacement of the fastener cartridge.

The driving surface formed by pinion gear 132 engages arcuate racks 108 such that reciprocal motion of trigger 102 rotates the pinion-spur-gear assembly 130 in both clockwise and counterclockwise directions. The driving surface formed by spur gear 134 engages a horizontal longitudinal rack 140 formed in the underside of rack rod 142 (as shown in FIG. 7). Rotation of spur gear 134 translates through the horizontal longitudinal rack 140, to longitudinal reciprocal motion of the rack rod 142.

With continued reference to FIG. 2, in conjunction with FIG. 3, rack rod 142 is longitudinally slidable within handle body 28 atop spur gear 134. A pair of rollers 144 are rotatably fixed relative to handle body portions 28L and 28R by pins 146 engaged in holes 148 formed on the interior of the handle body portions. Rollers 144 abut longitudinal shoulders 150 of rack rod 142 to prevent rack rod 81 from disengaging spur gear 134.

Rack rod 142 is provided with a longitudinal cylindrical shaft 152 having an axially mounted protruding stem 154 and bearing a push plug 156. Push plug 156 preferably has a chamfered distal tip and is configured and dimensioned to be received within a pair of transverse slots 158 formed distally of fingers 160 on a channel 162. Channel 162 is an elongated member having a substantially U-shaped cross-section and is slidably mounted within elongate body portion 24 for reciprocal longitudinal motion therein. Near a distal end of channel 162, a slot 164 is formed which is configured and dimensioned to interfit and engage a proximal end of flexible pusher members 166 at corresponding slots 168 formed therein. Pusher members 166 are preferably formed of a flexible resilient material, such as stainless steel, and are formed as thin bands to provide flexibility for articulation and strength for transmitting force. Flexible pusher members 166 are positioned adjacent one another and fastened together near proximal ends thereof, for example, by a pin 170 passing through transverse holes formed distally of slots 168. Each flexible pusher member 166 is provided with a raised bearing surface 172 formed at a distal end thereof, which bias against a proximal end of a camming sled 174. Sled 174 is preferably formed in a wedge shape and has side walls 176 forming camming surfaces which, as will be described in greater detail below, cam a plurality of individual staple pushers 178 slidably mounted in a replaceable staple cartridge 180 to eject staples therefrom.

A substantially S-shaped knife shank 182 is longitudinally oriented and has a distal hook portion to engage a transverse mounting surface formed on sled 174 to be pulled distally along therewith. A knife blade 184 is mounted on a proximal hook portion of knife shank 182 by any suitable known mounting techniques. Knife blade 184 follows camming sled 174 longitudinally along the length of staple cartridge 180 and between the newly formed rows of staples, as will be described in greater detail below.

The operation of the various subassembly features of surgical stapler 20 will now be described with reference to FIGS. 4A–8. With initial reference to FIGS. 4A and 4B, the articulating feature of fastening and cutting portion (or "fastener assembly") 26 is shown. In an initial or unarticulated condition (shown in phantom), articulation control lever 30 is positioned in a distalmost orientation corresponding to fastening and cutting portion 26 being substantially aligned with the central longitudinal axis surgical stapler 20. In this position exterior elongate section 30a of control lever 30 is generally aligned with the longitudinal axis of the instrument and the distal fastening assembly. In order to articulate the fastening and cutting portion 26 as shown in FIG. 4A, the user moves articulation control lever 30 proximally in the direction of Arrow "A" shown in FIG. 4B, such that articulation control lever 30 is moved outwardly away from rotation handle 32. Proximal movement of control lever 30 causes the lever to pivot about pin 34 and further causes pin 35' to move in slot 36a of link rod 36. This movement results in proximal movement of link rod 36 and causes the fastener assembly 26 to pivot about rivet 42. In the articulated position, axis "C'" of the fastener assembly is articulated at an angle Ø with respect to axis "C", and section 30a of lever 30 is oriented away from axis "C", thereby indicating articulation.

Therefore, by moving lever 30, the user is provided with a visual indication of the relative orientation of fastening and cutting portion 26 with respect to the longitudinal axis of the instrument.

Figure 6:
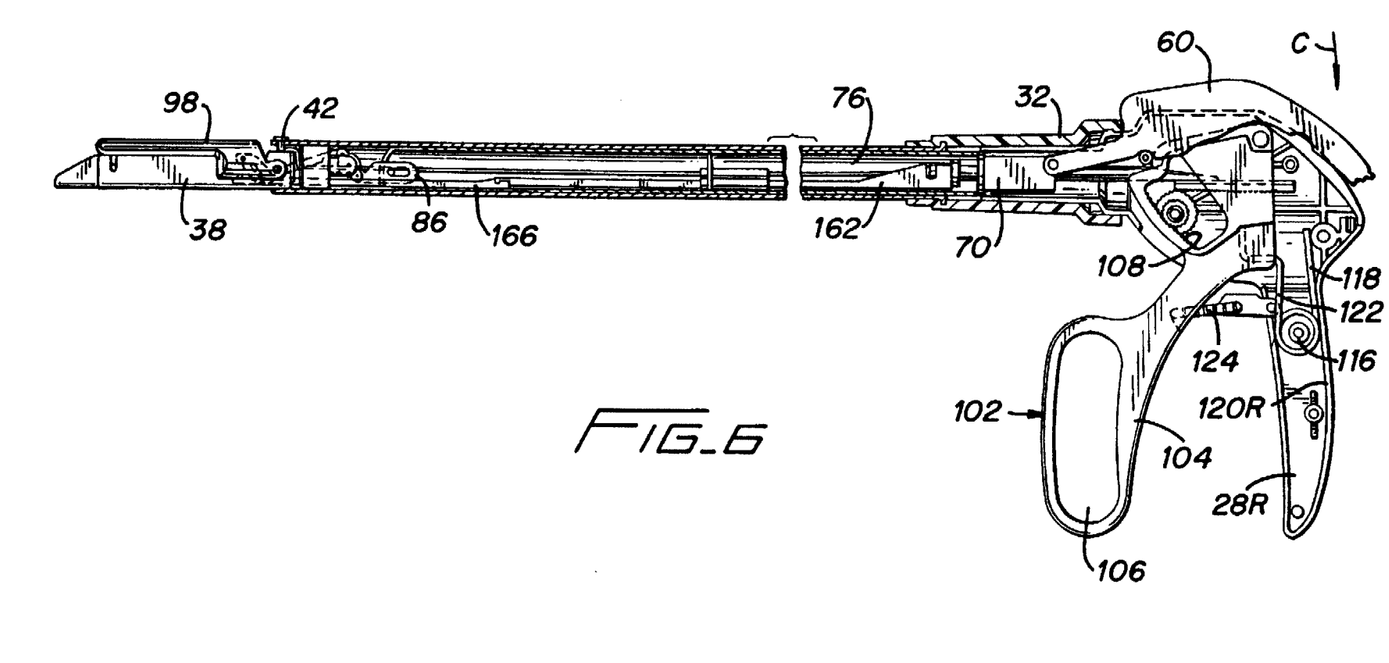
FIG. 6 is a side cross-sectional view, which illustrates the closing of the instrument's clamping mechanism.

Referring now to FIGS. 5, 5A and 6, the operation of the clamping feature of surgical stapler 20 will now be described in detail. Surgical instrument 20 is preferably initially oriented such that anvil 98 is in the clamped shut position as shown in FIG. 1. In this orientation, clamp approximation control lever 60 is oriented so that it is pivoted immediately adjacent handle body 28. When the user desires to open the clamp so as to position tissue between the fastener cartridge 118 and the anvil 98, clamp approximation lever 60 is lifted upwardly away from handle body 28 in the direction of Arrow "B" in FIG. 5. This motion causes proximal longitudinal motion of clamp pusher tube 72, which motion is translated by reverser link 92 into distal movement of flexible clamp links 94. Clamp cam 96 is, in turn, moved upwardly to open anvil 98. When it is desired to clamp anvil 98 in a closed position clamp approximation control lever 60 is simply pushed downwardly toward handle body 28, as indicated by Arrow "C" in FIG. 6, reversing the movements previously described.

With the tissue clamped between anvil 98 and fastener cartridge 118, the user, when prepared to fire the instrument, must first release safety 124 which is accomplished by simply pivoting safety 124 downwardly away from trigger 102 as shown in FIG. 7. Once safety 124 is released, the user then simply squeezes trigger 102 in the direction of Arrow "D" in FIG. 7, which drives rack rod 142 in a distal direction, thereby urging the interconnected firing channel member 162, flexible pushers 166, and camming sled 176 also in a distal direction to cam the fastener pushers 178 (FIG. 3) located in the fastener cartridge 118 and eject the staples therefrom.

Upon completion of firing the staples surgical stapler 20 may be reloaded with a new fastener cartridge as shown in FIG. 8 and reused again according to the above description.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. An apparatus for applying a plurality of surgical fasteners to body tissue comprising:
   a) a handle assembly;
   b) an elongated body extending from the handle assembly and defining a longitudinal axis;
   c) a cartridge housing pivotably connected to a distal end portion of the elongated body;
   d) a fastener cartridge containing a plurality of surgical fasteners and positionable in the cartridge housing;
   e) an anvil pivotally mounted adjacent relative to the cartridge housing and defining a fastener forming surface against which surgical fasteners are driven when ejected from the fastener cartridge, the anvil being pivotable relative to the cartridge housing between a first position in longitudinal alignment with the cartridge housing and a second position skewed relative to a longitudinal axis of the cartridge housing;

f) a fastener driving mechanism operatively associated with the fastener cartridge and actuatable from the handle assembly to eject fasteners from the fastener cartridge;

g) a single rod link member in direct operative association with the cartridge housing, which pivotably moves the cartridge housing between a first position in alignment with the longitudinal axis of the elongated body, and a second position out of alignment with the elongated body longitudinal axis; and h) a pivotable control lever in direct operative association with the single rod link member and pivotable between a position corresponding to the first position of the cartridge housing and a position corresponding to the second position of the cartridge housing, the relative pivotable position of the control lever providing visual indication of the position of the cartridge housing relative to the elongated body.

2. An apparatus according to claim 1, wherein the control lever is pivotable outwardly away from the handle.

3. An apparatus according to claim 1, wherein the elongated body is rotatably disposed on the handle body.

4. An apparatus according to claim 1, wherein the link is an elongated member extending through the elongated body and operatively connected to the control lever and to the cartridge housing.

5. An apparatus according to claim 1 further including a clamping mechanism operatively associated with the anvil, which moves the anvil relative to the cartridge housing to clamp tissue therebetween.

6. An apparatus according to claim 5, wherein the clamping mechanism includes a plurality of elongated flexible bands which flex upon movement of the cartridge housing from the first position to the second position.

7. An apparatus according to claim 6 wherein the clamping mechanism further includes a cam operatively associated with the anvil and the plurality of elongated flexible bands.

8. An apparatus according to claim 1, wherein the fastener driving mechanism includes a plurality of elongated flexible bands which flex upon movement of the cartridge housing from the first position to the second position.

9. An apparatus according to claim 8, wherein the fastener driving mechanism further includes a camming member adapted to urge the fasteners from the fastener cartridge.

10. An apparatus according to claim 9, wherein the camming member moves in a distal direction to urge the fasteners from the fastener cartridge.

11. An apparatus for applying a plurality of surgical fasteners to body tissue comprising:

a) a handle assembly;

b) an elongated body extending from the handle assembly and defining a longitudinal axis;

c) a cartridge housing pivotably connected to a distal end portion of the elongated body;

d) a fastener cartridge containing a plurality of surgical fasteners and positionable in the cartridge housing;

e) an anvil pivotally mounted relative to the cartridge housing and defining a fastener forming surface against which surgical fasteners are driven when ejected from the fastener cartridge, the anvil being pivotable relative to the cartridge housing between a first position in longitudinal alignment with the cartridge housing and a second position skewed relative to a longitudinal axis of the cartridge housing;

f) a clamping mechanism actuatable from the handle assembly to effect relative movement of the anvil and the cartridge housing to clamp tissue therebetween;

g) a fastener driving mechanism operatively associated with the fastener cartridge and actuatable from the handle assembly to eject fasteners from the fastener cartridge;

h) a single rod actuation member reciprocatingly moveable within the elongated body and in direct operative association with the cartridge housing, to pivotably move the cartridge housing between a first position in alignment with the longitudinal axis of the elongated body, and a second position out of alignment with the elongated body longitudinal axis; and i) a control lever in direct operative association with the single rod actuation member, the lever being pivotable between a position corresponding to the first position of the cartridge housing and a position corresponding to the second position of the cartridge housing.

12. An apparatus according to claim 11, wherein the control lever is pivotable outwardly away from the handle assembly, the relative pivotal position of the control lever providing the user with visual indication of the position of the cartridge housing relative to the elongated body.

13. An apparatus according to claim 11, wherein the elongated body is rotatably disposed on the handle assembly.

14. An apparatus according to claim 11, wherein the clamping mechanism includes a plurality of elongated flexible bands which flex upon movement of the cartridge housing from the first position to the second position.

15. An apparatus according to claim 14, wherein the clamping mechanism further includes a cam operatively connected to the plurality of elongated flexible bands and the anvil to facilitate opening and closing thereof.

16. An apparatus according to claim 11, wherein the fastener driving mechanism includes a plurality of elongated flexible bands which flex upon movement of the cartridge housing from the first position to the second position.

* * * * *